(12) United States Patent
Botts

(10) Patent No.: US 11,383,000 B2
(45) Date of Patent: Jul. 12, 2022

(54) AEROSOL STERILIZATION SURGICAL LAMP USING UV LIGHT AND VISIBLE LIGHT

(71) Applicant: Jason Bryce Botts, Germantown, TN (US)

(72) Inventor: Jason Bryce Botts, Germantown, TN (US)

(73) Assignee: Jason Bryce Botts, Germantown, TN (US)

( * ) Notice: Subject to any disclaimer, the term of this patent is extended or adjusted under 35 U.S.C. 154(b) by 100 days.

(21) Appl. No.: 16/915,338

(22) Filed: Jun. 29, 2020

(65) Prior Publication Data

US 2021/0402040 A1 Dec. 30, 2021

(51) Int. Cl.
*A61L 9/20* (2006.01)
*A61B 90/35* (2016.01)
(Continued)

(52) U.S. Cl.
CPC ............... *A61L 9/20* (2013.01); *A61B 90/35* (2016.02); *F21S 8/043* (2013.01); *F21V 21/26* (2013.01);
(Continued)

(58) Field of Classification Search
CPC .... A61L 9/20; A61L 2209/12; A61L 2209/14; A61B 90/35; F21S 8/043; F21V 21/26;
(Continued)

(56) References Cited

U.S. PATENT DOCUMENTS

| 5,910,291 A | * | 6/1999 | Skalla | ................... A61B 18/00 261/DIG. 26 |
| 8,454,197 B2 | | 6/2013 | Hauschulte et al. | |

(Continued)

FOREIGN PATENT DOCUMENTS

| CN | 205137274 U | 4/2016 |
| CN | 109404822 A | 3/2019 |

(Continued)

OTHER PUBLICATIONS

Anggoro, D., Budhi, S., Purnomo, A., & Megarani, D. V., "Evaluation of ultraviolet-C lamps sterilization in veterinary operating theatre," *ARSHI Veterinary Letters* 3(4): 75-76 (Nov. 2019).

(Continued)

*Primary Examiner* — David E Smith
(74) *Attorney, Agent, or Firm* — Sterne, Kessler, Goldstein & Fox P.L.L.C.

(57) ABSTRACT

The present disclosure provides a lamp for a medical operating area. The lamp includes a mounting assembly and a luminaire sterilization head. The luminaire sterilization head includes a vacuum, a first light source, and second light source. The vacuum generates a gas stream for evacuating a volume of the aerosol through the luminaire sterilization head. The first light source emits a visible light beam for illuminating the target. The second light source emits ultraviolet light waves along the gas stream for disinfecting the biological agent in the evacuated aerosol. The mounting assembly adjusts the separation distance between the luminaire sterilization head and the target of the medical procedure. The mounting assembly adjusts the orientation of the luminaire sterilization head to alter the angle of the visible light beam emitted by the first light source and the gas stream generated by the vacuum.

19 Claims, 11 Drawing Sheets

(51) Int. Cl.
*F21V 21/26* (2006.01)
*F21S 8/04* (2006.01)
*F21V 33/00* (2006.01)
*F21W 131/202* (2006.01)
*F21Y 113/10* (2016.01)
*F21Y 105/14* (2016.01)

(52) U.S. Cl.
CPC ....... *F21V 33/0068* (2013.01); *A61L 2209/12* (2013.01); *A61L 2209/14* (2013.01); *F21W 2131/202* (2013.01); *F21Y 2105/14* (2016.08); *F21Y 2113/10* (2016.08)

(58) Field of Classification Search
CPC ............. F21V 33/0068; F21Y 2105/14; F21Y 2113/10
See application file for complete search history.

(56) References Cited

U.S. PATENT DOCUMENTS

| | | | |
|---|---|---|---|
| 9,144,617 B2 | 9/2015 | Deng | |
| 9,662,409 B2* | 5/2017 | Rains, Jr | F21V 23/003 |
| 10,166,309 B2* | 1/2019 | Liao | C02F 1/008 |
| 2008/0188170 A1* | 8/2008 | Della Valle | A61B 90/40 |
| | | | 454/62 |
| 2010/0234794 A1* | 9/2010 | Weadock | A61G 13/108 |
| | | | 604/20 |
| 2012/0199003 A1* | 8/2012 | Melikov | A61L 9/20 |
| | | | 95/273 |
| 2019/0167833 A1* | 6/2019 | Yang | A61L 9/20 |
| 2020/0345905 A1* | 11/2020 | Lin | A61M 1/80 |
| 2021/0283423 A1* | 9/2021 | Anderson | A61N 5/0624 |
| 2021/0307873 A1* | 10/2021 | Faerber | A61B 50/33 |

FOREIGN PATENT DOCUMENTS

| | | | |
|---|---|---|---|
| CN | 209101130 U | * | 7/2019 |
| JP | 2014204901 A | * | 10/2014 |

OTHER PUBLICATIONS

Kim, D. K., & Kang, D. H., "UVC LED Irradiation Effectively Inactivates Aerosolized Viruses, Bacteria, and Fungi in a Chamber-Type Air Disinfection System," *Appl. Environ. Microbiol.*, 84(17): 1-11 (Sep. 2018).

Murrell, L. J., Hamilton, E. K., Johnson, H. B., & Spencer, M., "Influence of a visible-light continuous environmental disinfection system on microbial contamination and surgical site infections in an orthopedic operating room," *American Journal of Infection Control*, 47(7): 804-810 (Jul. 2019).

* cited by examiner

AEROSOL STERILIZATION SURGICAL LAMP USING UV LIGHT AND VISIBLE LIGHT

BACKGROUND

Field of the Invention

The present disclosure relates to a lamp for a medical procedural area, and more particularly to a lamp for illuminating a target of a medical procedure and sterilizing microbial aerosols airborne in the medical procedural area.

Background

Execution of some medical procedures, such as dental operations, oral surgeries, or procedures, leads to the generation of microbial aerosols containing various types of biological agents, such as bacteria, viruses, fungi, saliva droplets, tooth dusts, or pathogens. Exposure to these aerosolized biological agents can lead to the spread of infection and disease.

Thus, there is a need for a medical lamp that can effectively sterilize and evacuate the microbial aerosols from a medical procedural area, while illuminating the target site of the medical procedure.

BRIEF SUMMARY OF THE INVENTION

The present disclosure includes various embodiments of a lamp for a medical procedure area.

In accordance with one embodiment, a lamp for a medical procedure area comprises an arm and a luminaire sterilization head pivotably coupled to a distal end of the arm. In some embodiments, the luminaire sterilization head comprises a vacuum configured to generate a gas stream for evacuating a volume of the aerosol through the luminaire sterilization head, a first light source configured to emit a visible light beam for illuminating the target, and a second light source configured to emit ultraviolet light waves along the gas stream for disinfecting the biological agent in the evacuated aerosol. In some embodiments, wherein the luminaire sterilization head is configured to pivot about the distal end of the arm to adjust an angle of the visible light beam and an angle of the gas stream In some embodiments, the luminaire sterilization head includes a shroud. In some embodiments, the shroud comprises a perimeter wall defining a duct extending from a front end of the perimeter wall to a back end of the perimeter wall, and a face disposed at the front end of the perimeter wall.

In some embodiments, the first light source and the second light source are disposed along the face of the shroud. In some embodiments, the vacuum is disposed in the shroud, and the face defines an intake opening for drawing in the gas stream into the duct of the perimeter wall and the back end of the perimeter wall defines an exhaust opening for discharging the gas stream out of the duct.

In some embodiments, the first light source includes a set of first emitters configured to emit visible light and the second light source includes a set of second emitters configured to emit ultraviolet light waves. In some embodiments, the set of first emitters are concentrically arranged with respect to the set of second emitters. In some embodiments, the second slight source is configured to emit the ultraviolet light waves in a range from 200 nm to 230 nm In some embodiments, the luminaire sterilization head further comprises a filter disposed ahead of the vacuum, the filter configured to remove particulate matter suspended in the evacuated aerosol. In some embodiments, the vacuum comprises a fan and a motor. In some embodiments, the fan is configured to propel airflow at a volumetric flow rate between 100 ft$^3$/min and 1000 ft$^3$/min. In some embodiments, the luminaire sterilization head further includes a blower disposed rearward of the vacuum. In some embodiments, the blower is configured to generate an air curtain surrounding the gas stream generated by the vacuum.

In some embodiments, the arm comprises an articulation defining a pivot axis, the arm is configured to pivot about the pivot axis to adjust a separation distance between the luminaire sterilization head and the target. In some embodiments, the lamp includes a base coupled to the arm, the base is configured to be mounted to a ceiling. In some embodiments, the lamp includes a base coupled to the arm, the base is configured to move along the ground to adjust a separation distance between the luminaire sterilization head and the target.

In accordance with one embodiment, a luminaire sterilization head for illuminating a target and evacuating an aerosol containing a biological agent comprises a shroud, a vacuum, a first light source, and a second light source. In some embodiments, the shroud comprises a perimeter wall and a face, wherein the perimeter wall defines a duct extending from a front end of the perimeter wall to a back end of the perimeter wall. In some embodiments, the face is disposed at a front end of the perimeter wall and defining an intake opening for the duct. In some embodiments, the vacuum is disposed in the duct of the perimeter wall. In some embodiments, the vacuum is configured to generate a gas stream for evacuating the aerosol into the duct through the intake opening and discharging the evacuated aerosol out of the duct through the back end of the perimeter wall. In some embodiments, the first light source is disposed along the face of the shroud. In some embodiments, the first light source is configured to emit a visible light beam for illuminating the target. In some embodiments, the second light source is disposed along the face of the shroud. In some embodiments, the second light source is configured to emit ultraviolet light waves along the gas stream for disinfecting the biological agent in the evacuated aerosol.

In some embodiments, the first light source includes a set of first emitters configured to emit visible light and the second light source includes a set of second emitters configured to emit ultraviolet light waves. In some embodiments, the second set of emitters are disposed along a central position of the face, and the intake opening is disposed around the second set of emitters. In some embodiments, the intake opening is disposed along a central position of the face, and the set of first emitters and the second of second emitters are arranged in a circle formation around the intake opening. In some embodiments, the set of first emitters are concentrically arranged with respect to the set of second emitters. In some embodiments, the second slight source is configured to emit the ultraviolet light waves in a range from 200 nm to 230 nm.

In some embodiments, the luminaire sterilization head further comprises a filter disposed in the duct and located upstream of the vacuum, the filter configured to remove particulate matter suspended in the evacuated aerosol. In some embodiments, the luminaire sterilization head includes a user interface controller configured to activate and deactivate the second light source while the first light source remains activated for illuminating the target. In some embodiments, the air stream generated by the vacuum is coaxially arranged with respect to the visible light beam and the ultraviolet light waves. In some embodiments, the perimeter wall defines a peripheral passage extending around the duct. In some embodiments, the peripheral passage includes an inlet opening into the duct and disposed rearward of the vacuum. In some embodiments, the face defines an outlet opening for the peripheral passage. In some embodiments, the luminaire sterilization head further includes a blower disposed in the shroud and rearward of the vacuum. In some embodiments, the blower is configured to propel air flow through the peripheral passage and out of the outlet opening to generate an air curtain surrounding the gas stream generated by vacuum.

BRIEF DESCRIPTION OF THE DRAWINGS/FIGURES

The accompanying drawings, which are incorporated herein and form a part of the specification, illustrate the present disclosure and, together with the description, further serve to explain the principles thereof and to enable a person skilled in the pertinent art to make and use the same.

DETAILED DESCRIPTION OF THE INVENTION

Figure 1:
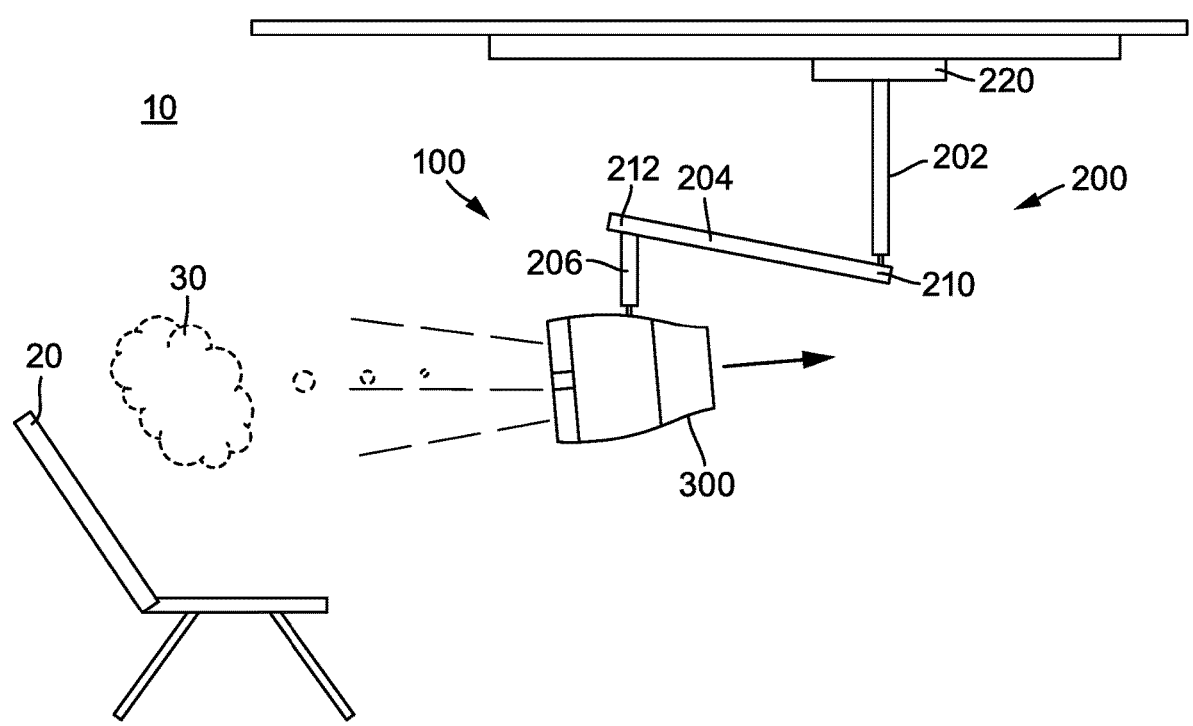
FIG. 1 shows a medial lamp disposed in a medical procedure area according to embodiments.

The present inventions will now be described in detail with reference to embodiments thereof as illustrated in the accompanying drawings, in which like reference numerals are used to indicate identical or functionally similar elements. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following examples are illustrative, but not limiting, of the present inventions. Other suitable modifications and adaptations of the variety of conditions and parameters normally encountered in the field, and which would be apparent to those skilled in the art, are within the spirit and scope of the inventions.

One attempt over the years to sterilize the medical procedural areas is providing ventilation equipment to evacuate microbial aerosols generated by the medical procedure. Ventilation equipment typically include a source for generating high-velocity air evacuation and a duct extending from the evacuation source towards the surgical site.

However, using an extension duct to remove microbial aerosol is not convenient and may obstruct the medical provider from executing the medical procedure properly. Moreover, combining the ventilation equipment with other medical equipment in the operating room does not allow the microbial aerosol to be effectively sterilized or prolong the time to fully sterilize the operating environment.

Accordingly, there is a need for a luminaire sterilization head that can effectively sterilize the microbial aerosols by concentrating ultraviolet irradiation along a gas stream that evacuates the microbial aerosol from the operating environment.

According to various embodiments described herein, the lamp of the present disclosure may overcome one or more of the deficiencies noted above by comprising a luminaire sterilization head that includes a vacuum, a first light source, and a second light source. In some embodiments, the vacuum may be configured to generate a gas stream for evacuating the aerosol through the luminaire sterilization head. In some embodiments, the first light source may be configured to emit a visible light beam for illuminating the target. In some embodiments, the second light source may be configured to emit ultraviolet light waves along the gas stream for disinfecting the biological agent in the evacuated aerosol.

Figure 2:
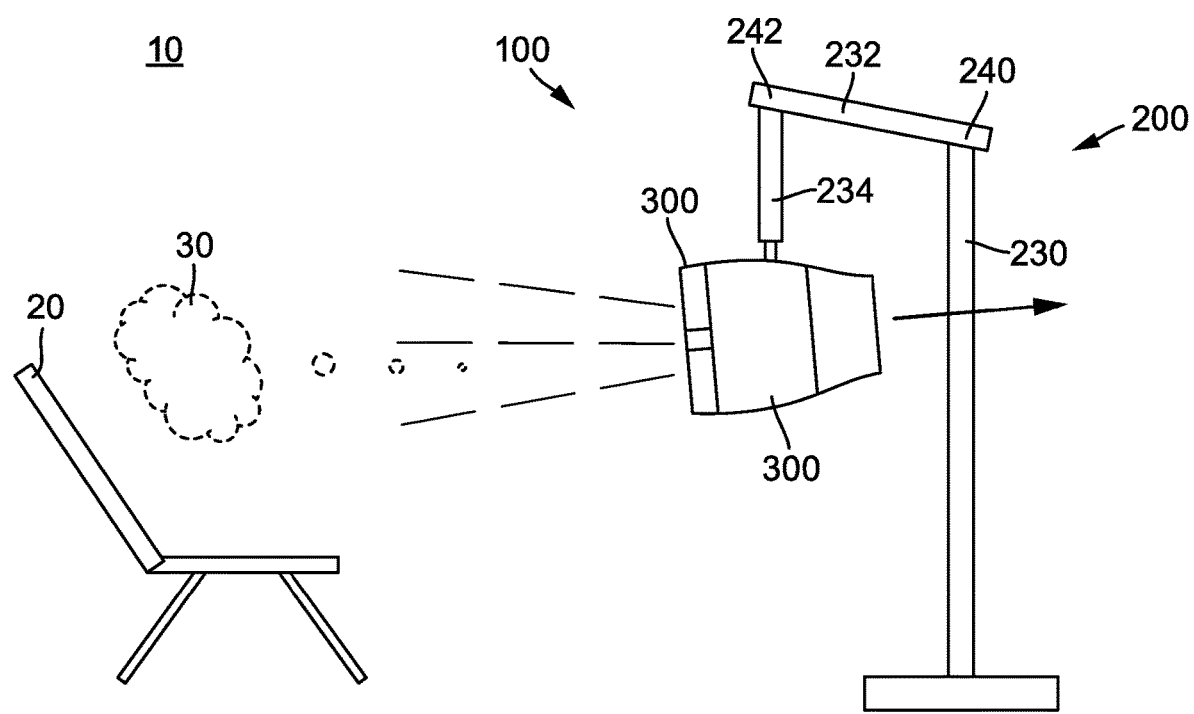
FIG. 2 shows a medial lamp disposed in a medical procedure area according to embodiments.

Embodiments will now be described in more detail with reference to the figures. With reference to FIGS. 1 and 2, for example, in some embodiments, a medical lamp 100 may include a mounting assembly 200 and a luminaire sterilization head 300. As shown in FIGS. 1 and 2, medical lamp 100 may be disposed in a medical procedure area 10 housing an operating chair 20 and an aerosol 30 containing a mixture of fluid (e.g., water, compressed air), one or more biological agents, and/or one or more particulate matters. For example, in some embodiments, medical procedure area 10 may be used for a dental procedure (e.g., extraction, crown preparation, endodontic treatment) of a patient disposed on operating chair 20, whereby the dental procedure generates a microbial aerosol 30 containing a biological agent, such as, for example, saliva, blood, tooth debris, virus, bacteria, fungi, protozoa, or other types of microorganisms.

In various embodiments, luminaire sterilization head 300 may be configured to simultaneously illuminate a target (e.g., the patient's mouth) and sterilize aerosol 30 through ultraviolet irradiation treatment and air filter removal at the target or an area adjacent or including the target. In various embodiments, the position of the luminaire sterilization head 300 with respect to the target may be adjusted (e.g., using mounting assembly 200), such that luminaire sterilization head 300 is allowed to move around the target in a lateral, longitudinal, or vertical direction, to maintain the luminaire sterilization head 300 within a predetermined separation distance from the target and/or at a predetermined angle with respect to the target.

In some embodiments, luminaire sterilization head 300 may be configured to emit a visible light beam focused on the target (e.g., a patient resting on operating chair 20) such that the target is sufficiently illuminated for a medical procedure. In some embodiments, luminaire sterilization head 300 may be configured to irradiate aerosol 30 with ultraviolet light waves, thereby disinfecting at least one of the biological agents suspended in aerosol 30. In some embodiments, luminaire sterilization head 300 may be configured to generate a gas stream drawing aerosol 30 toward luminaire sterilization head 300 such that at least a volume of aerosol 30 is evacuated through luminaire sterilization head 300. In some embodiments, luminaire sterilization head 300 may be configured to remove one or more particulate matter as the volume of aerosol 30 is evacuated through luminaire sterilization head 300, thereby filtering pathogens from the evacuated volume of aerosol 30. In some embodiments, luminaire sterilization head 300 may be configured to discharge sterilized, filtered exhaust air back into the medical procedure area 10, thereby ventilating medical procedure area 10 with sterilized, filtered air.

Figure 6:
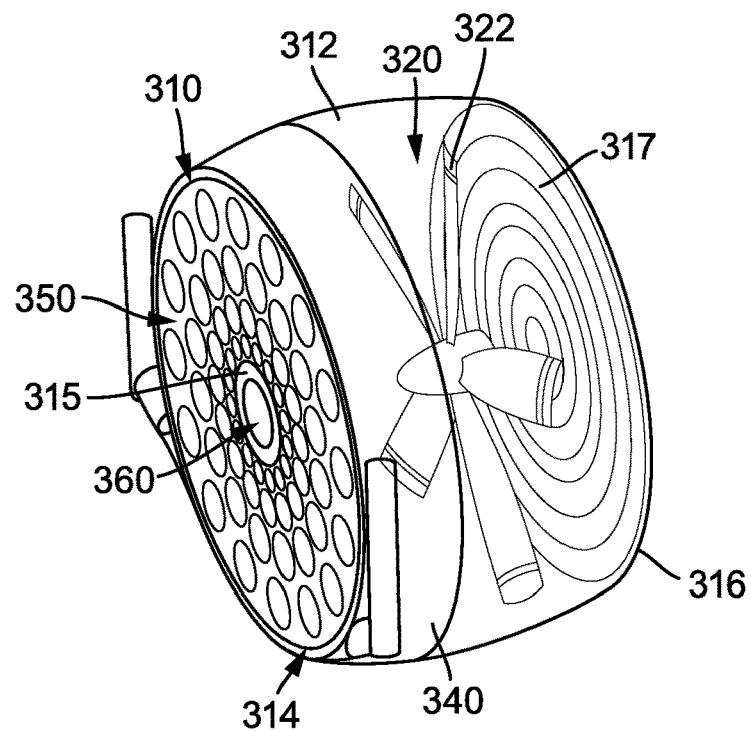
FIG. 6 shows a perspective view of a luminaire sterilization head, in which the perimeter wall is transparent for illustration purposes to show further details of the luminaire sterilization head, according to some embodiments.
Figure 7:
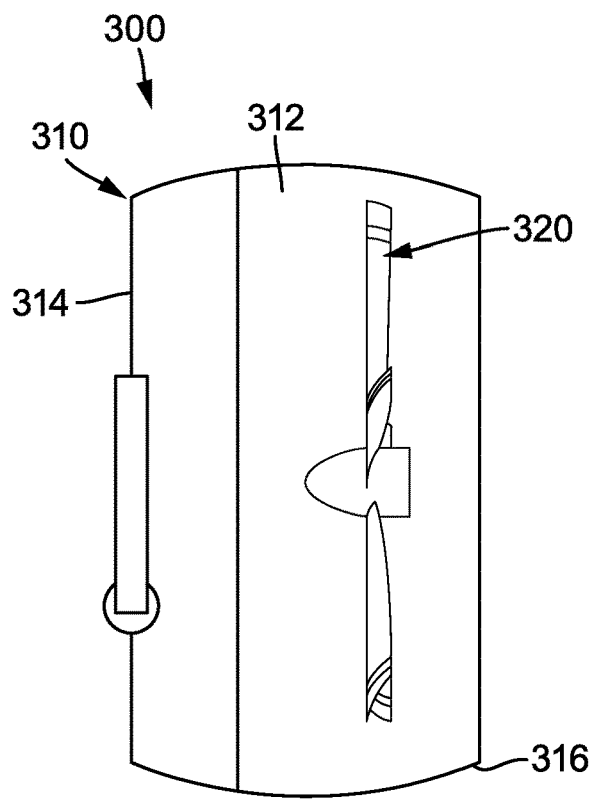
FIG. 7 shows a side view of a luminaire sterilization head, in which the perimeter wall is transparent for illustration purposes to show further details of the luminaire sterilization head, according to some embodiments.
Figure 8:
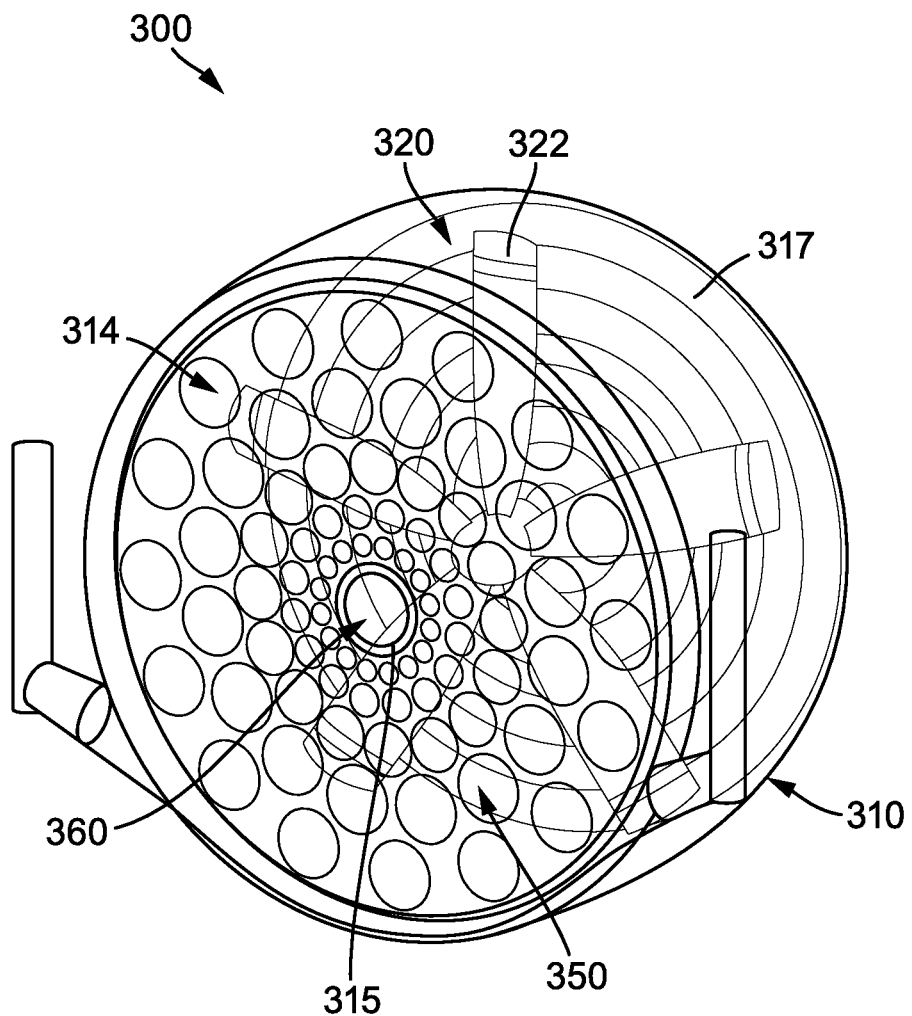
FIG. 8 shows a front perspective view a luminaire sterilization head, in which the perimeter wall and face are transparent for illustration purposes to show further details of the luminaire sterilization head, according to some embodiments.

In some embodiments, as shown in FIGS. 1-3B and 6-8, for example, luminaire sterilization head 300 may include a shroud 310. In some embodiments, shroud 310 may include a perimeter wall 312 defining a duct 318 extending along a longitudinal axis of perimeter wall 312. In some embodiments, shroud 310 may include a face 314 disposed at a front end 312A of perimeter wall 312. In some embodiments, face 314 may be configured to intake and direct air into duct 318. In some embodiments, shroud 310 may include an exhaust opening 316 disposed at a back end 312B of perimeter wall 312. In some embodiments, exhaust opening 316 may be configured to discharge air so that air may exit shroud 310 after passing through duct 318. In some embodiments, as shown in FIGS. 6 and 8, for example, shroud 310 may include a grid 317 disposed along exhaust opening 316 to obstruct a user's hand or damaging debris from entering shroud 310.

Figure 3A:
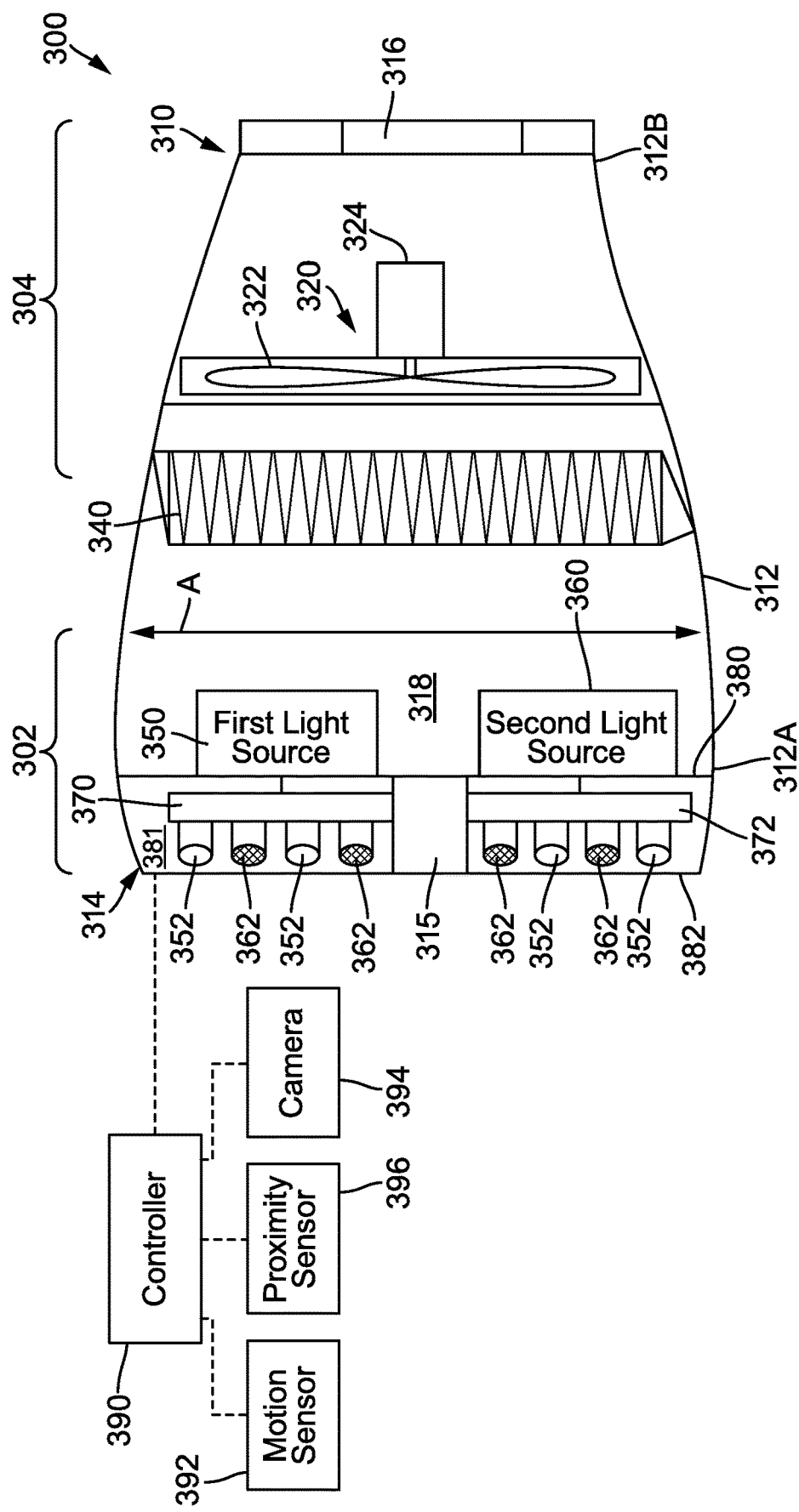
FIG. 3A shows a longitudinal cross-sectional schematic view of a luminaire sterilization head according to embodiments.
Figure 3B:
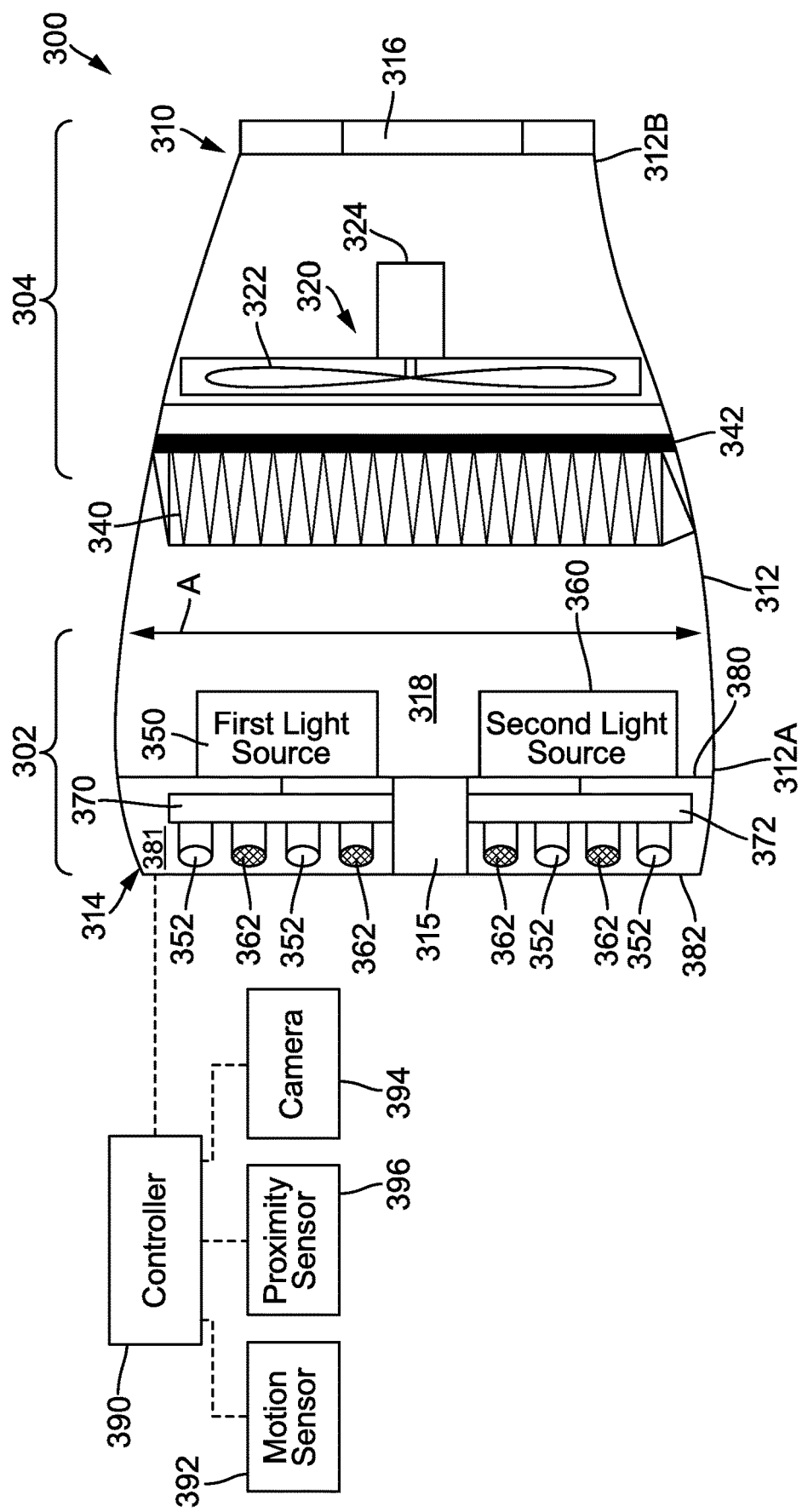
FIG. 3B shows a longitudinal cross-sectional schematic view of a luminaire sterilization head according to embodiments.

In some embodiments, a shape of perimeter wall 312 may be configured to promote air flow passing through duct 318. In some embodiments, as shown in FIGS. 3A-B for example, perimeter wall 312 may define a lateral transverse dimension A (e.g., a diameter) that increases along a front section 302 of shroud 310 and then decreases along a back section 304 of shroud 310 to promote air intake at front end 312A of perimeter wall 312 and propel airflow through back end 312B of perimeter wall 312. In some embodiments, as shown in FIGS. 3A-B and 7, for example, a surface of perimeter wall 312 may be sloped along a longitudinal direction, such that lateral transverse dimension A varies along the longitudinal axis of perimeter wall 312, to promote airflow through duct 318. In some embodiments, as shown in FIGS. 3A-B, for example, a lateral transverse dimension (e.g., a diameter) of front end 312A of perimeter wall 312 may be larger than lateral transverse dimension of back end 312B of perimeter wall 312. In some embodiments, as shown in FIG. 7 for example, the lateral transverse dimension of front end 312A of perimeter wall 312 may be equal to the lateral transverse dimension of back end 312B of perimeter wall 312. In some embodiments, the shape of perimeter wall 312 may be cylindrical or tubular such that lateral transverse dimension of perimeter wall 312 remains substantially constant along the longitudinal axis of perimeter wall 312. In some embodiments, as shown in FIG. 7, for example, front and back ends 312A, 312B of perimeter wall 312 may include a transverse dimension (e.g., a diameter) smaller than a transverse dimension A of perimeter wall 312.

Figure 9:
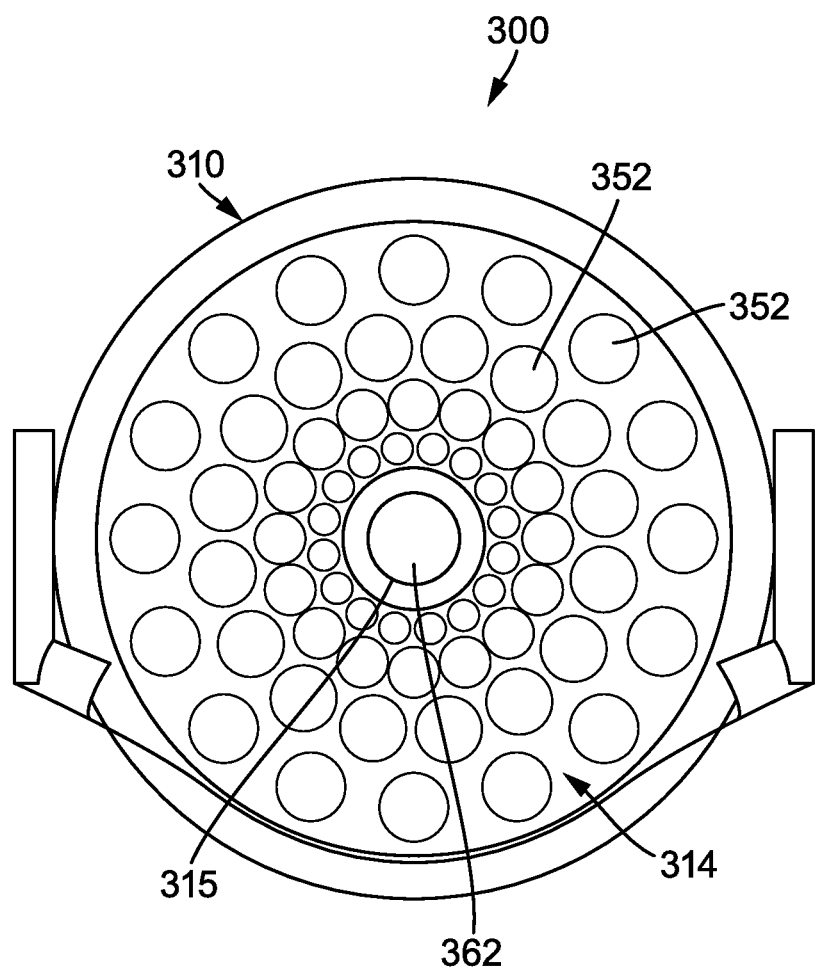
FIG. 9 shows a front view of a luminaire sterilization head according to embodiments.

In some embodiments, face 314 may partially enclose the front end of perimeter wall 312 and configured to hold one or more light sources for illuminating the target and sterilizing aerosol 30. In some embodiments, as shown in FIGS. 3A-B and 9, for example, face 314 may define a central intake opening 315 in fluid communication with duct 318. In some embodiments, as shown in FIGS. 3A-B, for example, central intake opening 315 may define a circular shape. In some embodiments, as shown in FIG. 9, for example, central intake opening 315 may define an annular shape. In some embodiments, face 314 may define a plurality of intake openings in fluid communication with duct 318. For example, face 314 may define, in one configuration, a central intake opening 315 and a plurality of peripheral intake openings disposed around central intake opening 315. In some embodiments, face 314 may define any number and arrangement of intake openings to promote air intake into duct 318 of shroud 310.

In some embodiments, as shown in FIGS. 3A-B and 6-8, for example, luminaire sterilization head 300 may include a vacuum 320 disposed in shroud 310. In some embodiments, vacuum 320 may be configured to generate a gas stream that draws gas through intake opening 315 of face 314 and discharge gas through exhaust opening 316. In some embodiments, vacuum 320 may be disposed in a back section 304 of shroud 310 proximate to exhaust opening 316. In some embodiments, vacuum 320 may be disposed in the center of shroud 310. In some embodiments, vacuum 320 may be disposed in front section 302 of shroud 310 proximate to face 314 of shroud 310.

In some embodiments, a vacuum 320 may include any component suitable for generating a stream of high gas velocity (e.g., a gas stream) that creates a substantial air pressure differential between duct 318 and the ambient air of medical procedure area 10 to draw ambient air into duct 318 via intake opening 315. In some embodiments, vacuum 320 may include a fan 322 extending transverse along duct 318 and configured to propel airflow in a longitudinal direction from the front end 312A toward back end 312B of perimeter wall 312, such that air, including evacuated aerosol 30, is pulled from intake opening 315 to exhaust opening 316. In some embodiments, an inlet of fan 322 is disposed rearward of one or more light sources and in fluid communication with intake opening 315 of face 314. In some embodiments, an outlet of fan 322 is disposed frontward of back end 312B of perimeter wall 312 and in fluid communication with exhaust opening 316. In some embodiments, fan 322 may be configured to generate a gas stream having a volumetric flow rate suitable for evacuating aerosol 30 from the medical procedure area 10. In some embodiments, fan 322 may generate a gas stream having a volumetric flow rate in a range of about 100 ft$^3$/min to about 1000 ft$^3$/min. In some embodiments, fan 322 may be an axial fan that includes a plurality of blades (e.g., hydro-mechanical stator blades) coupled to a rotary shaft. In some embodiments, fan 322 may be a centrifugal fan that includes a plurality of blades coupled to a rotary shaft. In some embodiments, vacuum 320 may include a motor 324 operatively linked to fan 322 and configured to propel angular rotation of fan 322. In some embodiments, motor 324 may receiver power supply from a power source, such as an AC current source (e.g., wall power outlet) or a battery disposed in shroud 310. In some embodiments, motor 324 may controlled by a controller (e.g., controller 390) operatively linked (e.g., wired-connection and/or wireless-connection) to luminaire sterilization head 300, such as the computer system shown in FIG. 10. In some embodiments, the rotational speed of fan 322 may be adjusted through pulse-width-modulation (e.g., duty cycle) of the power supply to motor 324.

In some embodiments, fan 322 of vacuum 320 may be disposed in a secondary location disposed outside shroud 310 (e.g., ceiling of medical procedure area 10 or a mobile cart), and vacuum 320 may include a duct extension extending from fan 322 to shroud 310. In some embodiments, the duct extension may include an outlet vent disposed at a predetermined location to maintain containment of airflow within medical procedure area 10.

In various embodiments, luminaire sterilization head 300 may include one or more filters disposed in shroud 310 and configured to remove particulate matter from the evacuated volume of aerosol passing through duct 318. In some embodiments, luminaire sterilization head 300 may include a filter 340 disposed in shroud 310 and extending transverse to duct 318. In some embodiments, filter 340 is disposed frontward of the inlet of fan 322 and rearward of one or more light sources. In some embodiments, filter 340 is configured to remove particulate matter from the evacuated volume of aerosol while passing through duct 318. In some embodiments, filter 340 is a high-efficiency particulate air (HEPA) filter configured to meet regulatory and/or laboratory standards (e.g., American Society of Mechanical Engineers) for purifying air. For example, in some embodiments, filter 340 is configured to trap 99.97% of particulates 0.3 microns or larger in the gas stream passing through duct 318. In some embodiments, filter 340 may include any structure, such as electrostatic precipitator, carbon filter, foam, fibrous materials, perforated sheets, and/or meshes of fiberglass, plastic fibers, etc., suitable for removing particulate matter from the evacuated aerosol 30.

In some embodiments, as shown in FIG. 3B, for example, luminaire sterilization head 300 may include a secondary filter 342 disposed in shroud 310 and extending transverse to duct 318. In some embodiments, secondary filter 342 may be disposed frontward of filter 340 and configured to serve as a pre-filter trapping larger-sized particulate matter from the evacuated volume of aerosol passing through duct 318. In some embodiments, secondary filter 342 may be disposed rearward of filter 340 and frontward of vacuum 320. In some embodiments, secondary filter 342 may be configured to remove finer-sized particulate matter and eliminate odors from the evacuated volume of aerosol passing through duct 318. In some embodiments, secondary filter 342 may be comprised of one or more granular impregnated alumina-based materials, activated carbon-based materials, and/or impregnated activated carbon-based materials (e.g., activated bituminous-coal carbon, charcoal) configured to absorb orders and chemicals, such as mercury vapors. In some embodiments, luminaire sterilization head 300 may include a filter assembly disposed in shroud 310, in which the filter assembly includes a pre-filter, filter 340 disposed rearward of the pre-filter and comprised of a HEPA filter, and secondary filter 342 disposed rearward of filter 340 and comprised of an activated carbon filter. Additional filters and/or other combinations of filters may be used.

In some embodiments, luminaire sterilization head 300 may include one or more light sources to emit both a visible light beam suitable for illuminating a target and ultraviolet light waves suitable for germicidal irradiation treatment, such as disinfecting biological agents suspended in aerosol 30. In some embodiments, the one or more light sources may be disposed on shroud 310 frontward of filter 340 and vacuum 320.

In some embodiments, luminaire sterilization head 300 may include a first light source 350 configured to emit a visible light beam for illuminating the target. In some embodiments, first light source 350 is configured to emit light waves with a spectrum profile in a range between about 400 nm and about 750 nm. In some embodiments, the color index of light waves emitted by first light source 350 may include any color suitable for illuminating a target, such as, for example, a white light.

In some embodiments, luminaire sterilization head 300 may include a second light source 360 configured to emit ultraviolet light waves suitable for germicidal irradiation treatment. In one embodiment, second light source 360 may be configured to emit ultraviolet light waves with a spectrum profile in a range of about 200 nm to 280 nm (e.g., UV-C spectrum) such that emitted ultra light waves are suitable for disinfecting the biological agents suspended in aerosol 30. In some embodiments, second light source 360 may be configured to adjust the wavelength of the emitted ultraviolet light waves at one or more operating ranges suited for a particular purpose (e.g., sterilizing aerosol, sterilizing room surfaces). In some embodiments, the wavelength of the ultraviolet light waves emitted by second light source 360 may be set to a first operating range (e.g., 200 nm to 230 nm) suitable for breaking down molecular bonds within the biological agents suspended in aerosol 30 while not providing harmful exposure to a patient. For example, in one embodiment, the first operating range for ultraviolet light waves emitted by second light source 360 may range between 207 nm to 222 nm such that emitted ultraviolet light waves are suitable for disinfecting the biological agents suspended in aerosol 30 while not providing harmful exposure to a patient. In some embodiments, the wavelength of the ultraviolet light waves emitted by second light source 360 may be set to a second operating range suitable for sterilizing surfaces of an operating room. For example, in one embodiment, the second operating range for ultraviolet light waves emitted by second light source 360 may range between 231 nm and 280 nm. In some embodiments, the color index of ultraviolet light waves emitted by second light source 360 may include any color suitable for germicidal irradiation treatment.

In some embodiments, luminaire sterilization head 300 may include a controller 390 operatively linked to first light source 350 and second light source 360. In some embodiments, controller 390 may be linked to first light source 350 and second light source 360 by a wired connection. In some embodiments, controller 390 may be linked to first light source 350 and second light source 360 by a wireless connection (e.g., NFC, Bluetooth, Local Area Network). In some embodiments, controller 390 may include any component, such as the system shown in FIG. 10, suitable for controlling operation of first light source 350 and second light source 360. In some embodiments, controller 390 may be configured to selectively activate and/or deactivate first light source 350 and second light source 360. In some embodiments, controller 390 may be configured to adjust light output (lumens) of first light source 350 and second light source 360.

In some embodiments, controller 390 may be configured to adjust the wave lengths of the ultraviolet light waves emitted by second light source 360 to a predetermined operating range. For example, in some embodiments, controller 390 may be configured to set second light source to a first mode, in which the second light source 360 emits ultraviolet light waves at the first operating range (e.g., 200 nm to 230 nm) suitable for breaking down molecular bonds within the biological agents suspended in aerosol 30 while not providing harmful exposure to a patient. In some embodiments, controller 390 may be configured to set second light source 360 to a second mode, in which the second light source 360 emits ultraviolet light waves at the second operating range (230 nm to 280 nm) suitable for sanitizing the room surfaces of the medical procedure area 10.

In some embodiments, controller 390 may be configured to selectively switch second light source 360 between the first mode and the second mode based on one or more conditions. For example, in some embodiments, controller 390 may be configured to set second light source 360 to operate in the first mode and the second mode based on predetermined time periods or a programmed schedule. In some embodiments, controller 390 may be configured to switch second light source between the first mode and the second mode based on the detection of human presence in medical procedure area 10. For example, in some embodiments, controller 390 may be operatively linked (e.g., wired-connection and/or wireless-connection) to a motion sensor 392 disposed in medical procedure area 10. In some embodiments, motion sensor 392 may be configured to detect presence of a human in medical procedure area 10 and transmit a detection signal to controller 390. In some embodiments, controller 390 may be configured to switch second light source 360 from operating in the second mode to the first mode upon receiving the detection signal from motion sensor 392, such that the second light source 360 emits ultraviolet light waves at an operating range (e.g., 200 nm to 230 nm) that is safe for human exposure. In some embodiments, controller 390 may be configured to switch second light source from operating in the first mode to the second mode after not receiving a detection signal from motion sensor 392 for a predetermined period of time (e.g., 15 minutes without detection of human presence). In some embodiments, motion sensor 392 may include at least one of a passive infrared sensor, a microwave sensor, and/or radar sensor suitable for detecting presence of a human in medical procedure area 10.

Figure 4:
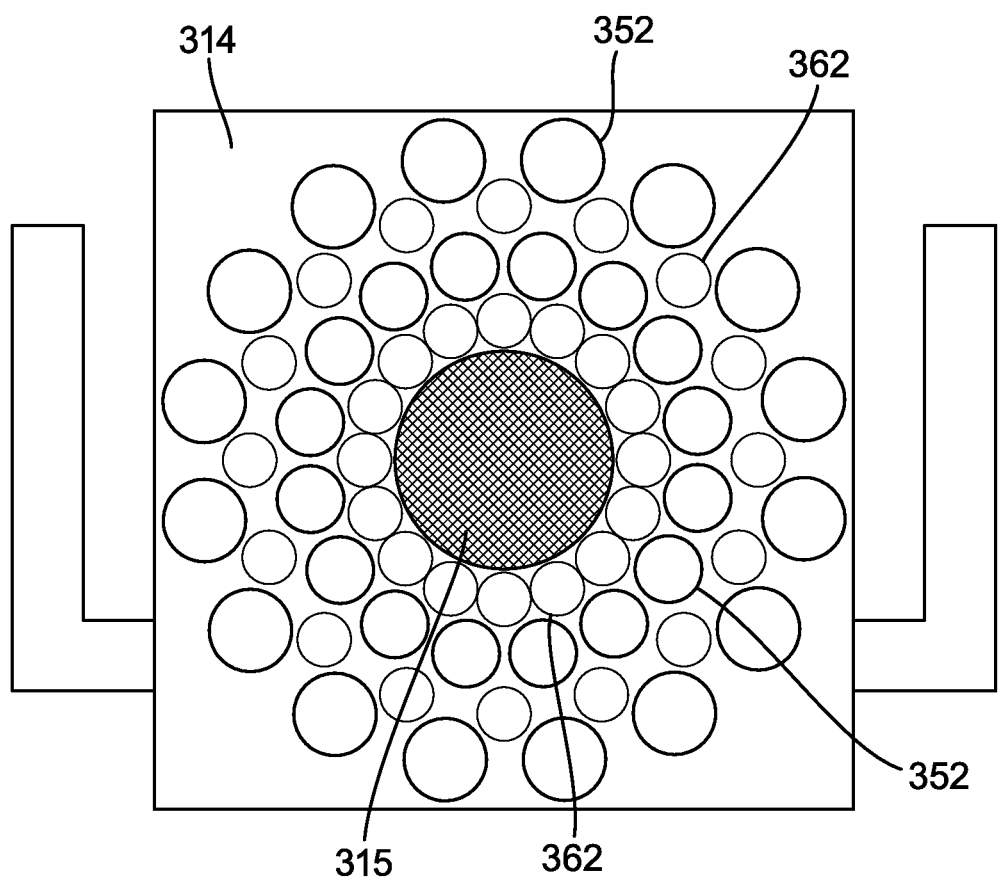
FIG. 4 shows a front schematic view of a luminaire sterilization head according to embodiments.
Figure 5:
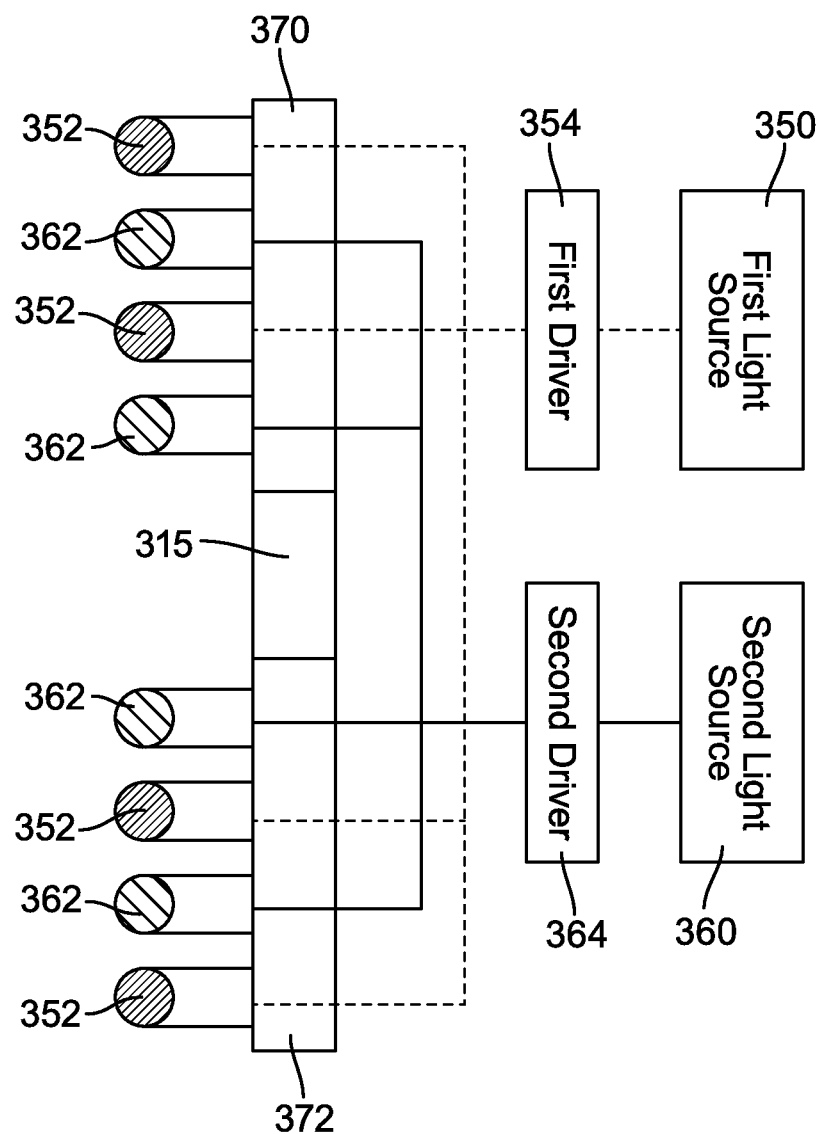
FIG. 5 shows a schematic view of a first light and a second light source configured to be integrated with a sterilization luminaire head according to embodiments.

In some embodiments, as shown in FIGS. 3-5, for example, first light source 350 may include a first set of emitters 352, in which each emitter 352 is configured to emit visible light (e.g., light waves between about 400 nm and 700 nm). In some embodiments, the first set of emitters 352 comprise an array of light emitting diodes (LED) connected to one or more printed circuit boards 370, 372. In some embodiments, the first set of emitters 352 may include other illuminating devices, such as for example, halogen incandescent bulbs and/or fluorescent lights. In some embodiments, first light source 350 may include a first driver circuit 354 operatively connected to the first set of emitters 352. In some embodiments, first driver circuit 354 may be configured to control the intensity, duration, and frequency of light waves of the first set of emitters 352 by adjusting the current output to the first set of emitters 352 and/or using pulse width modulation (e.g., short duty cycle). In some embodiments, first driver circuit 354 may include any type of circuitry component, such as for example, series resistors, current regulators (e.g., MOSFET, LDO), capacitors, diodes, amplifier, transistor, and integrated circuits, suitable for regulating voltage and current supply to the first set of emitters 352. In some embodiments, first driver circuit 354 of first light source 350 may receiver power supply from a power source, such as an AC current source (e.g., wall power outlet) or a battery disposed in shroud 310. In some embodiments, first driver circuit 354 may be controlled by controller 390, such as the system shown in FIG. 10.

In some embodiments, as shown in FIGS. 3-5, for example, second light source 360 may include a second set of emitters 362, in which each emitter 362 is configured to emit ultraviolet light waves (e.g., light waves between about 200 nm and 240 nm). In some embodiments, the second set of emitters 362 comprise an array of light emitting diodes (LED) connected to one or more printed circuit boards 370, 372. In some embodiments, second light source 360 may include a second driver circuit 364 operatively connected to the second set of emitters 362. In some embodiments, second driver circuit 364 may be configured to control the intensity, duration, and frequency of light waves of the second set of emitters 362 by adjusting the current output to the second set of emitters 362 and/or using pulse width modulation (e.g., short duty cycle). In some embodiments, second driver circuit 364 may include any type of circuitry component, such as for example, series resistors, current regulators (e.g., MOSFET, LDO), capacitors, diodes, amplifiers, transistors, and integrated circuits, which are suitable for regulating voltage and current supply to the second set of emitters 362. In some embodiments, second driver circuit 364 of second light source 360 may receiver power supply from a power source, such as an AC current source (e.g., wall power outlet) or a battery disposed in shroud 310. In some embodiments, second driver circuit 364 may be controlled by controller 390, such as the system shown in FIG. 10.

In some embodiments, face 314 may include any structure suitable for housing and securing first light source 350 and/or second light source 360 to perimeter wall 312 of shroud 310. In some embodiments, face 314 may include a base plate 380 partially enclosing front end 312A of perimeter wall 312 and defining central intake opening 315. In some embodiments, the base plate 380 may be secured to the first set of emitters 352 and second set of emitters 362.

In some embodiments, face 314 may include any type of optical equipment suitable for focusing, diffusing, and/or transmitting the generated light output from first light source 350 and/or second light source 360. In some embodiments, face 314 may include a cover lens 382 covering the first set of emitters 352 and second set of emitters 362. In some embodiments, cover lens 382 may be coupled to periphery of base plate 380. In some embodiments, cover lens 382 may define a hemispherical shape such that cover lens 382 defines an optical cavity 384 for transmitting light waves. In some embodiments, cover lens 382 may be configured to transmit light waves emitted from the first set of emitters 352 and ultraviolet light waves emitted from the second set of emitters 362.

In some embodiments, face 314 may include a collimator lens or a reflection cup associated with one or more emitters 352, 362 to focus the light waves emitted by emitters 352, 362. In some embodiments, the collimated lens and/or reflection cup may include any shape suitable for focusing light waves emitted from emitters 352, 362. In some embodiments, collimated lens may define a circular truncated cone shape or a cylindrical tube shape. In some embodiments, collimated lens may be comprised of any material suitable for focusing light waves emitted from emitters 352, 362. In some embodiments, the collimated lens and/or reflection cup may be comprised of silicon oxide (e.g., silica) and/or polymethyl methacrylate (e.g., PMMA). In some embodiments, the collimated lenses and/or reflection cup associated with the second set of emitters 362 may further include optical filters configured to output ultraviolet light wave at a predetermined bandwidth (e.g., 200 nm to 240 nm). In some embodiments, the dimensions of the collimated lens and/or reflection cups may vary along the face 314. For example, in some embodiments, the transverse dimension (e.g., diameter) of collimated lens and/or reflection cups disposed along a central region of the face plate 314 may be less than the transverse dimension of collimated lens and/or reflection cups disposed along a peripheral region of the face 314. In some embodiments, the dimensions of the collimated lens and/or reflection cups may be uniform along the face 314.

In some embodiments, the number of emitters 352 in the first set may be adjusted based on the optical power suitable for generating a sufficient intensity of visible light to illuminate the target. In some embodiments, the number of emitters 362 in the second set may be adjusted based on the optical power suitable for generating a sufficient intensity of ultraviolet irradiation suitable for germicidal treatment of aerosol 30.

In some embodiments, the first set of emitters 352 may be arranged in any geometrical pattern and/or formation suitable for generating a visible beam spread suitable for illuminating the target. For example, in some embodiments, the formation of emitters 352 in the first set may be configured to illuminate a beam spread suitable for a medical procedure. In some embodiments, the second set of emitters 362 may be arranged in any geometrical pattern and/or formation suitable for transmitting ultraviolet light waves in an coaxial arrangement with the gas stream generated by vacuum 320. For example, in some embodiments, the second set of emitters 362 may be located in a formation that concentrates ultraviolet irradiation along a central region of the beam spread illuminated by the first set of emitters 352. In some embodiments, the second set of emitters 362 may be configured to focus the emitted ultraviolet light waves upon the biological agents suspended in the volume of aerosol 30 that is pulled by the gas stream generated by vacuum 320.

In some embodiments, as shown in FIG. 4, for example, the first set of emitters 352 and the second set of emitters 362 may be arranged in circular formation around central intake opening 315. In some embodiments, the first set of emitters 352 may be concentrically arranged with respect to the second set of emitters 362. In some embodiments, the first set of emitters 352 may be disposed in multiple rows that are arranged in a circular formation, and the second set of emitters 362 may each be disposed in multiple rows that are arranged in circular formation. In some embodiments, the rows of the first set of emitters 352 and the rows of the second set of emitters 362 are alternatingly arranged in a radial direction from the central portion of plate 314. In some embodiments, the spacing between the first set of emitters 352 and the second set of emitters 362 may be configured to provide a symmetrical pattern of emitters 352, 362.

In some embodiments, as shown in FIG. 9, for example, the second set of emitters 362 may be disposed in a circular formation at about a central position of face 314. In some embodiments, an annular-shaped central intake opening 315 may be disposed around the second set of emitters 362 disposed about the central position of face 314. In some embodiments, the first set of emitters may be disposed around central intake opening 315 and the second set of emitters 362. In some embodiments, the first set of emitters 352 may be disposed in multiple rows that are arranged in a circular formation. In some embodiments, the circular-shaped rows of emitters 352 in the first set may be concentrically arranged with respect to the centrally-located second set of emitters 362. In some embodiments, the spacing between the first set of emitters 352 may be configured to provide a symmetrical pattern of emitters 352. In some embodiments, the second set of emitters 362 may include one or more emitters 362 disposed inside shroud 310. For example, in some embodiments, the second set of emitters 362 may include emitters 362 disposed along interior surface of perimeter wall 312 such that evacuated volume of aerosol 30 passing through duct 318 is exposed to additional ultraviolet irradiation treatment after being admitted through intake opening 315.

In some embodiments, the first set of emitters 352 and/or the second set of emitters 362 may be operatively connected to one or more actuators configured to rotate or move the first set of emitters 352 and the second set of emitters 362 along face 314 to adjust the orientation and pattern formation of the first set of emitters 352 and the second set of emitters 362. By adjusting the orientation and formation of emitters 352, 362, the one or more actuators may be configured to adjust the dimensions of the irradiation target site and/or adjust the angle of light waves emitted from first light source 350 and second light source 360. In some embodiments, the one or more actuators may include a motor (e.g., servomotor, linear motor) and a gear assembly operatively connected to the first set of emitters 352 and the second set of emitters 362.

In some embodiments, controller 390 may be operatively connected (e.g., wired-connection, wireless connection) to the one or more actuators to control movement of emitters 352, 362. In some embodiments, controller 390 may adjust the movement of emitters 352, 362 based on feedback to maintain emitted light waves at a particular target site or move the light waves from an obstacle. For example, in some embodiments, controller 390 may be operatively connected (e.g., wired connection and/or wireless connection) to a camera 394 configured to capture images of a target site and provide feedback video signals to controller 390. In some embodiments, controller 390 may be operatively linked to a proximity sensor 396 to detect presence of objects within proximity of luminaire sterilization head 300 and transmit a feedback warning signal to controller 390 to indicate when an object is within a predetermined distance of luminaire sterilization head 300. In some embodiments, controller 390 may be configured to determine whether an object is obstructing light waves emitted by emitters 352, 362 based on feedback video signals transmitted from camera 394 and/or feedback warning signals transmitted from proximity sensor 396. In some embodiments, upon receipt of the feedback signals, controller 390 may be configured to transmit a command signal to the one or more actuators to adjust orientation and/or pattern formation of the first set of emitters 352 and the second set of emitters 362.

In some embodiments, controller 390 may be operatively linked (e.g., wired-connection and/or wirelessly-connected) to other medical equipment, such as, for example, electrocautery unit, laser, dental hand piece, etc., disposed in medical procedure area 10. In some embodiments, controller 390 may be configured to activate/deactivate vacuum 320, first light source 350, and/or second light source 360 in tandem with the operation status of the other medical equipment in medical procedure area 10. For example, in some embodiments, controller 390 may be configured to keep second light source 360 and/or vacuum 320 activated for a predetermined time period (e.g., 1 second to 5 seconds) after other medical equipment have been switched off so that any aerosols generated by the medical equipment may be sterilized and filtered by luminaire sterilization head 300. In some embodiments, controller 390 may be set in a stand-by mode such that controller 390 is configured to activate first light source 350, second light source 360, and/or vacuum 320 when detecting that at least one of the medical equipment has been activated for a medical procedure. In some embodiments, luminaire sterilization head 300 may include an operating status display (e.g., LED light) indicating the operating status (e.g., on or off) of second light source 360 so that a user is aware of any potential exposure to emitted ultraviolet light waves.

Figure 11:
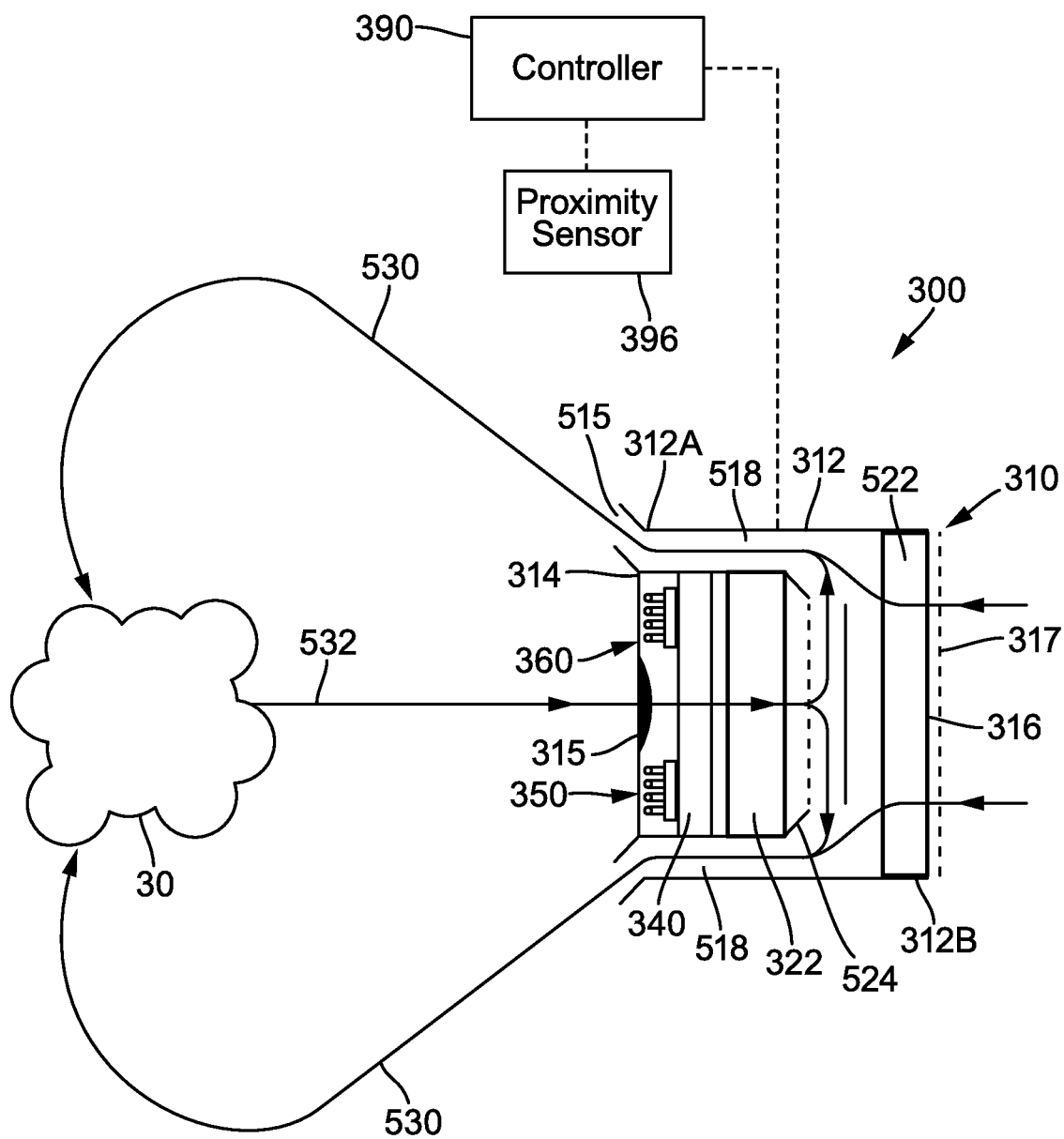
FIG. 11 shows a longitudinal cross-sectional schematic view of a luminaire sterilization head according to embodiments.

In some embodiments, as shown in FIG. 11, luminaire sterilization head 300 may be configured to redirect evacuated, filtered air from the outlet of fan 322 toward front end 312A of perimeter wall 312 such that a positive pressure air curtain (e.g. a jet stream of air) is generated along a perimeter of a target site or zone. In some embodiments, as shown in FIG. 11, perimeter wall 312 may define a peripheral passage 518 disposed around duct 318. In some embodiments, peripheral passage 518 defines an inlet opening into duct 318 and disposed rearward of fan 322 and proximate to a back end 312B of perimeter wall 312. In some embodiments, a portion of perimeter wall 312 may be extruded to form peripheral passage 518. In some embodiments, shroud 310 may include an interior wall coaxially arranged with respect to perimeter wall 312 to define peripheral passage 518 extending between perimeter wall 312 and the interior wall. In some embodiments, a portion of peripheral passage 518 (e.g., portion of peripheral passage 518 disposed at front end 312A of perimeter wall 312) may be angled away from the longitudinal axis of shroud 310, such as by 15° to 30°. In some embodiments, a portion of peripheral passage 518 is coaxially arranged with respect to duct 318. In some embodiments, face 314 may include an outlet opening 515 (e.g., annular-shaped opening) in fluid communication with peripheral passage 518.

In some embodiments, luminaire sterilization head 300 may include a blower 522 configured to pull gas through exhaust opening 316 and propel gas through peripheral passage 518 and out of outlet opening 515. In some embodiments, blower 522 may include any suitable component (e.g., axial fan or centrifugal fan operatively connected to a motor) suitable for pulling gas through exhaust opening 316 and propelling gas flow through peripheral passage 518 and out of outlet opening 515. In some embodiments, blower 522 is configured to generate a jet stream of air flowing out of outlet opening 515. In some embodiments, a volume of the jet stream flowing out of outlet opening 515 includes air sterilized by second light source 360 and filtered by filter 340. In some embodiments, luminaire sterilization head 300 may include one or more baffles 524 disposed at outlet of fan 322 to redirect gas pulled through duct 318 into peripheral passage 518.

In some embodiments, as shown in FIG. 11, the gas propelled out of outlet opening 515 via blower 522 may generate positive pressure air curtain 530 along the perimeter of a target site (e.g., aerosol 30 cloud) and the gas pulled through duct 318 by fan 322 may generate a negative pressure gas stream 532 disposed at central zone of the target site. In some embodiments, the combination of the pressure air curtain 530 and negative pressure gas stream 532 form a target recirculation zone, in which aerosol 30 is evacuated from the target recirculation zone and filtered, sterilized air is circulated back into the target recirculation zone. In some embodiments, fan 322 and blower 522 of luminaire sterilization head 300 may be configured to maintain a predetermined volume of air with the target zone by generating a recirculation pattern, thereby effectively reducing the outflow of aerosols outside the target zone and partially isolating the target zone from external contamination. In some embodiments, blower 522 may be configured to add air volume and acceleration to the air curtain 530 discharged at face 314 of shroud 310.

In some embodiments, controller 390 may be operatively linked (e.g., wired connection and/or wireless connection) to blower 522. In some embodiments, controller 390 may be configured to control fan speed of blower 522 and/or fan 322 based on feedback distance signals transmitted from proximity sensor 396. In some embodiments, proximity sensor 396 may be configured to detect a separation distance from a target site and/or target zone to face 314. In some embodiments, controller 390 may be configured to calculate variable fan speeds for fan 322 and/or blower 522 (e.g., fan 322 set at a first rotation speed, blower 522 set at a second rotation speed) based on feedback distance signals from proximity sensor 396 so that the target recirculation zone would be most effectively placed in relation to the desired target site. In some embodiments, luminaire sterilization head 300 may be optimally positioned (e.g., slightly distal) with respect to the target site or target zone so that aerosol 30 could be enveloped by positive pressure air curtain 530 and pulled toward luminaire sterilization head 30 via the negative pressure gas stream 532.

In various embodiments, mounting assembly 200 may be configured to adjust the position of luminaire sterilization head 300 with respect to the target to optimize ultraviolet irradiation treatment and air filter removal, while keeping the visible light beam focused on the target. In some embodiments, mounting assembly 200 may configured to modify a separation distance between luminaire sterilization head 300 and the target by positioning the luminaire sterilization head 300 closer to and/or further away from the target. In some embodiments, mounting assembly 200 may position luminaire sterilization head 300 proximate to the target, such that the separation distance between luminaire sterilization head 300 and the target is set within a predetermined distance, such as from about two ft. to four ft. from the target. In some embodiments, mounting assembly 200 may be configured to modify an orientation of the luminaire sterilization head 300 to adjust the angle of the visible light beam and an angle of the gas stream. In some embodiments, mounting assembly 200 may adjust the orientation of luminaire sterilization head 300 by tilting luminaire sterilization head 300 up and down and/or rotating luminaire sterilization head 300 in any angular direction. In some embodiments, mounting assembly 200 may be configured to move luminaire sterilization head 300 in any direction (disposed to the front, back, or the side of the patient) to adjust the position of the luminaire sterilization head 300 accordingly with respect to the target of the medical procedure.

In some embodiments, mounting assembly 200 may be configured to retrofit luminaire sterilization head 300 to an existing light fixture or lamp in medical procedure area 10, such as a track light or a surgical lamp in an operating room.

In some embodiments, as shown in FIG. 1, for example, mounting assembly 200 may be configured to mount to a ceiling 40 of medical procedure area 10 (e.g., as track light) such that luminaire sterilization head 300 is suspended from ceiling 40. In some embodiments, as shown in FIG. 2, for example, mounting assembly 200 may be to move along the floor of medical procedure area 10.

In some embodiments, mounting assembly 200 may include a plurality of arms pivotably and/or rotatably coupled together by one or more articulations and operatively connected to luminaire sterilization head 300 to adjust the position of the luminaire sterilization head 300 with respect to the target (e.g., space proximate to chair 20). In some embodiments, the one or more articulations include any structure, such as, for example, hinges, bearings, ball joint, etc., suitable for allowing angular rotation of at least one arm.

In some embodiments, as shown in FIG. 1, for example, mounting assembly 200 may include a first arm 202, a second arm 204, and a third arm 206. In some embodiments, first arm 202 may be pivotably and/or rotatably coupled to second arm 204 via a first articulation 210, such that second arm 204 is configured to pivot or rotate about a pivot axis defined by first articulation 210. In some embodiments, third arm 206 may be pivotably and/or rotatably coupled to second arm 204 by a second articulation 212, such that third arm 206 may pivot or rotate about a pivot axis defined by second articulation 212. In some embodiments, third arm 206 may be pivotably and/or rotatably coupled to luminaire sterilization head 300. In some embodiments, luminaire sterilization head 300 may be configured to pivot about a distal end of third arm 206 to adjust an angle of the visible light beam and an angle of the gas stream generated by vacuum 320. In some embodiments, the distal end of third arm 206 may include a universal joint, a yoke (e.g., a pair of arms received around perimeter wall 312), or any other structure suitable (e.g., combination of bearings, journal) for providing pivoting motion by the luminaire sterilization head 300. In some embodiments, mounting assembly may include a track base 220 configured to be mounted to the ceiling of medical procedure area 10. In some embodiments, track base 220 may be configured to move along ceiling of medical procedure area 10 to adjust the position of luminaire sterilization head 300 with respect to a target. In some embodiments, track base 220 may be configured to rotate to adjust angular orientation of luminaire sterilization head 300.

In some embodiments, mounting assembly 200 may include a lamp post 230, a first arm 232, and a second arm 234. In some embodiments, first arm 232 may be pivotably and/or rotatably coupled to lamp post 230 by a first articulation 240, such that first arm 232 may pivot or rotate about a pivot axis defined by first articulation 240. In some embodiments, second arm 234 may be pivotably and/or rotatably coupled to first arm 232 by a second articulation 242, such that second arm 234 may pivot or rotate about a pivot axis defined by second articulation 242. In some embodiments, second arm 234 may be pivotably and/or rotatably coupled to luminaire sterilization head 300. In some embodiments, luminaire sterilization head 300 may be configured to pivot about a distal end of second arm 234 to adjust an angle of the visible light beam and an angle of the gas stream generated by vacuum 320. In some embodiments, the distal end of second arm 234 may include a universal joint, a yoke (e.g., a pair of arms received around perimeter wall 312), or any other structure suitable (e.g., combination of bearings, journal) for providing pivoting motion by the luminaire sterilization head 300. In some embodiments, lamp post 230 may be fixed to an object (e.g., chair 20) disposed in medical procedure area 10. In some embodiments, as shown in FIG. 2, for example, mounting assembly may include a base 250 coupled to lamp post 230. In some embodiments, base 250 may be configured to move along the floor of medical procedure area 10 to adjust position of luminaire sterilization head 300 with respect to the target.

Figure 10:
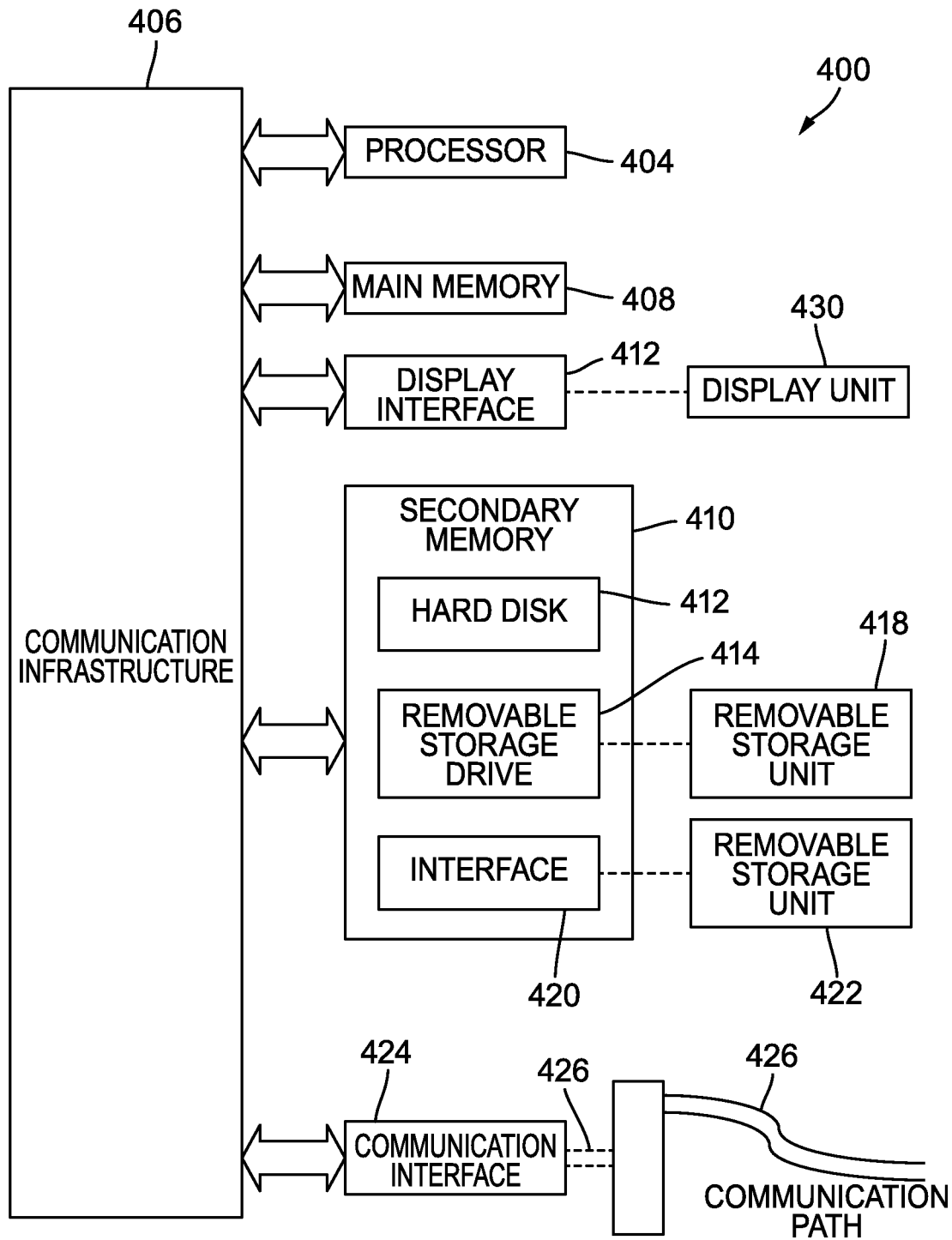
FIG. 10 shows a schematic block diagram of an exemplary computer system in which embodiments may be implemented.

FIG. 10 illustrates an exemplary computer system 400 in which embodiments, or portions thereof, may be implemented as computer-readable code. For example, aspects of the control protocols discussed herein (e.g., any control protocol associated with controller 390) that may be implemented in one or more computer systems include, but are not limited to, controlling power output to a motor of fan to adjust rotational speed of a fan and/or blower, controlling a driver circuit of a first light source to adjust the intensity, duration, wave length, and frequency of light waves emitted by the first light source, controlling a driver circuit of a second light source to adjust the intensity, duration, wave length, and frequency of light waves emitted by the second light source, and selectively activating/deactivating the first and second light sources, may be implemented in computer system 400 using hardware, software, firmware, tangible computer readable media having instructions stored thereon, or a combination thereof and may be implemented in one or more computer systems or other processing systems.

If programmable logic is used, such logic may execute on a commercially available processing platform or a special purpose device. One of ordinary skill in the art may appreciate that embodiments of the disclosed subject matter can be practiced with various computer system configurations, including multi-core multiprocessor systems, minicomputers, and mainframe computers, computer linked or clustered with distributed functions, as well as pervasive or miniature computers that may be embedded into virtually any device.

For instance, at least one processor device and a memory may be used to implement the above described embodiments. A processor device may be a single processor, a plurality of processors, or combinations thereof. Processor devices may have one or more processor "cores."

Various embodiments of the inventions may be implemented in terms of this example computer system 400. After reading this description, it will become apparent to a person skilled in the relevant art how to implement one or more of the inventions using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 404 may be a special purpose or a general purpose processor device. As will be appreciated by persons skilled in the relevant art, processor device 404 may also be a single processor in a multi-core/multiprocessor system, such system operating alone, or in a cluster of computing devices operating in a cluster or server farm. Processor device 404 is connected to a communication infrastructure 406, for example, a bus, message queue, network, or multi-core message-passing scheme.

Computer system 400 also includes a main memory 408, for example, random access memory (RAM), and may also include a secondary memory 410. Secondary memory 410 may include, for example, a hard disk drive 412, or removable storage drive 414. Removable storage drive 414 may include a floppy disk drive, a magnetic tape drive, an optical disk drive, a flash memory, a Universal Serial Bus (USB) drive, or the like. The removable storage drive 414 reads from and/or writes to a removable storage unit 418 in a well-known manner. Removable storage unit 418 may include a floppy disk, magnetic tape, optical disk, etc. which is read by and written to by removable storage drive 414. As will be appreciated by persons skilled in the relevant art, removable storage unit 418 includes a computer usable storage medium having stored therein computer software and/or data.

Computer system 400 (optionally) includes a display interface 402 (which can include input and output devices such as keyboards, mice, etc.) that forwards graphics, text, and other data from communication infrastructure 406 (or from a frame buffer not shown) for display on display unit 430.

In alternative implementations, secondary memory 410 may include other similar means for allowing computer programs or other instructions to be loaded into computer system 400. Such means may include, for example, a removable storage unit 422 and an interface 420. Examples of such means may include a program cartridge and cartridge interface (such as that found in video game devices), a removable memory chip (such as an EPROM, or PROM) and associated socket, and other removable storage units 422 and interfaces 420 which allow software and data to be transferred from the removable storage unit 422 to computer system 400.

Computer system 400 may also include a communication interface 424. Communication interface 424 allows software and data to be transferred between computer system 400 and external devices. Communication interface 424 may include a modem, a network interface (such as an Ethernet card), a communication port, a PCMCIA slot and card, or the like. Software and data transferred via communication interface 424 may be in the form of signals, which may be electronic, electromagnetic, optical, or other signals capable of being received by communication interface 424. These signals may be provided to communication interface 424 via a communication path 426. Communication path 426 carries signals and may be implemented using wire or cable, fiber optics, a phone line, a cellular phone link, an RF link or other communication channels.

In this document, the terms "computer program medium" and "computer usable medium" are used to generally refer to media such as removable storage unit 418, removable storage unit 422, and a hard disk installed in hard disk drive 412. Computer program medium and computer usable medium may also refer to memories, such as main memory 408 and secondary memory 410, which may be memory semiconductors (e.g. DRAMs, etc.).

Computer programs (also called computer control logic) are stored in main memory 408 and/or secondary memory 410. Computer programs may also be received via communication interface 424. Such computer programs, when executed, enable computer system 400 to implement the embodiments as discussed herein. In particular, the computer programs, when executed, enable processor device 404 to implement the processes of the embodiments discussed here. Accordingly, such computer programs represent controllers of the computer system 400. Where the embodiments are implemented using software, the software may be stored in a computer program product and loaded into computer system 400 using removable storage drive 414, interface 420, and hard disk drive 412, or communication interface 424.

Embodiments of the inventions also may be directed to computer program products comprising software stored on any computer useable medium. Such software, when executed in one or more data processing device, causes a data processing device(s) to operate as described herein. Embodiments of the inventions may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

The foregoing description of the specific embodiments will so fully reveal the general nature of the invention(s) that others can, by applying knowledge within the skill of the art, readily modify and/or adapt for various applications such specific embodiments, without undue experimentation, without departing from the general concept of the present invention(s). Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A lamp for a medical procedure area, comprising:
an arm; and
a luminaire sterilization head pivotably coupled to a distal end of the arm, the luminaire sterilization head comprising:
 a vacuum disposed in the luminaire sterilization head and configured to generate a gas stream for evacuating a volume of an aerosol disposed in the medical procedure area through the luminaire sterilization head,
 a first light source configured to emit a visible light beam for illuminating a target disposed in the medical procedure area,
 a second light source configured to emit ultraviolet light waves along the gas stream for disinfecting a biological agent in the evacuated aerosol,
 an intake opening disposed on the luminaire sterilization head for receiving the gas stream with the evacuated aerosol into the luminaire sterilization head, and
 an exhaust opening disposed on the luminaire sterilization head for discharging sterilized air out of the luminaire sterilization head and into the medical procedural area,
a controller operatively linked to the vacuum, the first light source, and the second light source, the controller configured to selectively activate and deactivate the vacuum, the first light source, and the second light source, wherein in response to receiving a feedback signal, the controller is configured to maintain activation of the vacuum and the second light source for a predetermined period of time after deactivating the first light source,
wherein the luminaire sterilization head is configured to pivot about the distal end of the arm to adjust an angle of the visible light beam and an angle of the gas stream.

2. The lamp of claim 1, wherein the luminaire sterilization head includes a shroud, the shroud comprising:
a perimeter wall defining a duct extending from a front end of the perimeter wall to a back end of the perimeter wall, and
a face disposed at the front end of the perimeter wall.

3. The lamp of claim 2, the first light source and the second light source are disposed along the face of the shroud.

4. The lamp of claim 2, wherein the vacuum is disposed in the shroud, and the intake opening is disposed on the face for receiving the gas stream into the duct of the perimeter wall and the exhaust opening is disposed at the back end of the perimeter wall for discharging the sterilized air out of the duct.

5. The lamp of claim 1, wherein the first light source includes a set of first emitters configured to emit visible light waves and the second light source includes a set of second emitters configured to emit ultraviolet light waves.

6. The lamp of claim 5, wherein the set of first emitters are concentrically arranged with respect to the set of second emitters.

7. The lamp of claim 1, wherein the second light source is configured to emit the ultraviolet light waves in a range from 200 nm to 250 nm.

8. The lamp of claim 1, wherein the luminaire sterilization head further comprises a filter disposed ahead of the vacuum, the filter configured to remove particulate matter suspended in the evacuated aerosol.

9. The lamp of claim 1, wherein the luminaire sterilization head further comprises a blower disposed rearward of the vacuum, the blower configured to generate an air curtain surrounding the gas stream generated by the vacuum.

10. The lamp of claim 1, wherein the vacuum comprises a fan and a motor, the fan is configured to propel airflow at a volumetric flow rate between 100 ft3/min and 1000 ft3/min.

11. The lamp of claim 1, further comprising a user interface configured to generate the feedback signal to the controller to deactivate the first light source and maintain activation of the vacuum and the second light source for the predetermined period of time.

12. The lamp of claim 1, wherein the controller is in communication with a medical equipment device disposed in the medical procedure area, and when becoming deactivated, the medical equipment device is configured to generate the feedback signal to the controller to deactivate the first light source and maintain activation of the vacuum and the second light source for the predetermined period of time.

13. A luminaire sterilization head for illuminating a target and evacuating an aerosol containing a biological agent, comprising:
a shroud comprising a perimeter wall and a face, wherein the perimeter wall defines a duct extending from a front end of the perimeter wall to a back end of the perimeter wall, and the face is disposed at a front end of the perimeter wall and defining an annular-shaped intake opening for the duct;
a vacuum comprising a fan disposed in the duct of the perimeter wall, the fan configured to generate a gas stream for evacuating the aerosol into the duct through the intake opening and discharging the evacuated aerosol out of the duct through the back end of the perimeter wall;
a first light source disposed along the face of the shroud and outside of the annular-shaped intake opening, the first light source configured to emit a visible light beam for illuminating the target; and
a second light source disposed along a central position of the face of the shroud such that the annular-shaped intake opening is disposed around the second light source, the second light source configured to emit ultraviolet light waves along the gas stream for disinfecting the biological agent in the evacuated aerosol.

14. The luminaire sterilization head of claim 13, wherein the first light source includes a set of first emitters configured to emit visible light waves and the second light source includes a set of second emitters configured to emit ultraviolet light waves.

15. The luminaire sterilization head of claim 13, wherein the second slight source is configured to emit the ultraviolet light waves in a range from 200 nm to 230 nm.

16. The luminaire sterilization head of claim 13, wherein the luminaire sterilization head further comprises a filter disposed in the duct and located upstream of the vacuum, the filter configured to remove particulate matter suspended in the evacuated aerosol.

17. The luminaire sterilization head of claim 13 further comprising a user interface controller configured to activate and deactivate the second light source while the first light source remains activated for illuminating the target.

18. The luminaire sterilization head of claim 13, wherein the perimeter wall defines a peripheral passage extending around the duct, the peripheral passage includes an inlet opening into the duct and disposed rearward of the vacuum, and the face defines an outlet opening for the peripheral passage, the luminaire sterilization head further comprises:
a blower disposed in the shroud and rearward of the vacuum, the blower configured to propel air flow through the peripheral passage and out of the outlet opening to generate an air curtain surrounding the gas stream generated by vacuum.

19. A lamp for a medical procedure area, comprising:
an arm;
a luminaire sterilization head pivotably coupled to a distal end of the arm, the luminaire sterilization head comprising:
a vacuum comprising a fan disposed in the luminaire sterilization head, the fan configured to generate a gas stream for evacuating a volume of an aerosol disposed in the medical procedure area through the luminaire sterilization head,
a blower disposed in the luminaire sterilization head and rearward of the fan, the blower configured to generate an air curtain surrounding the gas stream in the medical procedural area,
an intake opening disposed on the luminaire sterilization head for receiving the gas stream with the evacuated aerosol into the luminaire sterilization head,
an outlet opening disposed on the luminaire sterilization head, the outlet opening surrounding the intake opening for directing the air curtain around the gas stream,
a first light source configured to emit a visible light beam for illuminating a target disposed in the medical procedure area, and a second light source configured to emit ultraviolet light waves along the gas stream for disinfecting a biological agent in the evacuated aerosol, wherein the luminaire sterilization head is configured to pivot about the distal end of the arm to adjust an angle of the visible light beam and an angle of the gas stream, wherein the second light source is arranged at the intake opening to direct the emitted ultraviolet light waves along a section of the gas stream prior to entering through the intake opening.

* * * * *